United States Patent [19]

Gutierrez

[11] Patent Number: 5,553,325
[45] Date of Patent: Sep. 10, 1996

[54] HAT WITH ADJUSTABLE DUAL VISOR

[76] Inventor: Shelley S. Gutierrez, 324 Regal Dr., Laredo, Tex. 78041

[21] Appl. No.: 354,498

[22] Filed: Dec. 12, 1994

[51] Int. Cl.⁶ .................................................. A42B 1/20
[52] U.S. Cl. .................................... 2/171; 2/12; 2/171.03
[58] Field of Search ........................... 2/6.3, 6.4, 6.7, 2/10, 11, 12, 15, 171, 171.03, 175.1, 175.2, 195.1, 209.12; D2/865, 872, 873, 876, 879, 882, 883, 884, 886, 887, 893

[56] References Cited

U.S. PATENT DOCUMENTS

| | | |
|---|---|---|
| D. 56,990 | 1/1921 | Place .............................................. 2/171 |
| D. 284,328 | 6/1986 | Bieber . |
| 566,326 | 8/1896 | Kirschner . |
| 630,707 | 8/1899 | Jacobson . |
| 716,258 | 12/1902 | Maass . |
| 911,432 | 2/1909 | Pachner . |
| 1,525,115 | 2/1925 | Behm . |
| 1,716,719 | 6/1929 | Christopher . |
| 2,462,258 | 2/1949 | Dannenberg . |
| 2,735,109 | 2/1956 | Feldman . |
| 4,793,006 | 12/1988 | Dawson . |
| 5,007,110 | 4/1991 | Gilbert . |
| 5,271,099 | 12/1993 | Lin ................................................ 2/10 |

*Primary Examiner*—Diana Biefeld
*Attorney, Agent, or Firm*—Akin, Gump, Strauss, Hauer & Feld, L.L.P.

[57] ABSTRACT

An apparatus for partially shading the eyes of an intended user from excessive sunlight is disclosed. A dual visor hat has one generally stationary visor and a second visor that is detachably secured to the first visor. The hat has an air permeable, flexible, crescent-shaped member disposed between, and connected in hinged relation to, the first and second visors. Detaching the second visor from the first visor will extend the crescent shaped member downward, thereby positioning the second visor obliquely over the eyes of the intended user.

11 Claims, 5 Drawing Sheets

HAT WITH ADJUSTABLE DUAL VISOR

FIELD OF THE INVENTION

The invention relates generally to a hat with an adjustable visor. In particular, the invention relates to a hat with multiple visors providing varying degrees of shade for the eyes of an intended user.

BACKGROUND OF THE INVENTION

Hats with brims or visors are widely worn by golfers, tennis players, baseball players, hunters and farm workers. Those hats generally fit over the upper portion of the head, and the lower edge of the hat extends down in proximity to the tops of the ears. Those hats may have an open crown area to provide ventilation to the upper head portion of the intended user. Those hats normally have a visor attached to the hat's lower forward edge. The visor normally extends forward about two and one-half to four inches, with three inches being about average. The visor has a general width of about six to eight inches, with seven inches being about average. The construction of the visor is usually one or more layers of cloth juxtaposed and sewn about a stiffening material such as cardboard. The cardboard provides rigidity to the visor.

The purpose of the visor is to protect the face of the user against excessive sunlight that can cause sunburn and may harm the eyes. While the normal visor generally provides acceptable protection against various elements of nature, under certain circumstances the ordinary visor is inadequate to provide a desired degree of protection. In the morning or late in the day when the sun is low in the sky, ordinary visors do not provide the desired amount of shade to protect the eyes.

Sunburn to the general head and face of humans resulting from high intensity sunlight is well known. The sun's harmful ultraviolet rays cause painful sunburn even on cloudy days. Guarding against painful sunburn and skin cancer caused by those harmful rays has become a major health concern. Appropriate clothing is necessary to shield or shade the head and upper body when in direct sunlight or during cloudy sky periods. That clothing may include suitable protective garments and hats.

Hats with visors, in general, will shade the crown of the head, and the visor will provide some relief to the direct sunlight on the eyes of the intended user. The hat will function as intended depending on the position of the sun relative to the user. The user of any hat will find it necessary to constantly adjust the visor of the hat to accommodate the varying positions of the sun during the day. The user may have difficulty in reducing sun exposure because, to be effective throughout the day, the hat must extend over the eyes and severely limit the user's vision.

The art of adjustable-visor hats yields many examples. An example is U.S. Pat. No. 566,326 to Kirshner. Kirshner discloses a hat that has a variable-length visor. That variable-length visor achieves shading or protection for the eyes as the sun occupies progressively lower azimuthal angles in the sky. That manner of protection is limited to the times of day when the sun is nearly or directly overhead. That type of protection does nothing when the sun is on the horizon during the periods of sunrise or sunset.

U.S. Pat. No. 630,707 to Jacobson discloses a hat with a permanently hinged visor. The visor portion is a screen-type material that allows the user to see through the screen in the direction of travel, thereby necessarily passing sunlight. That particular type of hat-visor combination serves to protect the user from wind, dust and the like, while the user is moving rapidly forward, but does not protect the user from excessive sunlight.

U.S. Pat. No. 716,258 to Maass discloses a hat with a variable-length visor attached to the main visor by a plurality of nuts and bolts. Those bolts, when loosened, freely slide in provided guide slots, enabling the variable-length visor to be extended, thereby providing required protection from the sun. When a suitable position of the visor is obtained, the nuts are tightened to secure the visor in place.

U.S. Pat. No. 911,432 to Pachner discloses a hat with a transparent visor. Using this hat requires rotating the visor from a storage place inside the hat to a position extending outward from the front portion of the hat. The hat also has a holding flap attached to its front portion. The holding flap has a securing snap on its forward edge that will secure the transparent visor in a position above the eyes of the user. When the snap is not in use, the transparent visor adjusts to its lowest position over the eyes of the user, thereby greatly reducing the visibility of the user.

U.S. Pat. No. 4,793,006 to Dawson discloses a hat with a rigid primary visor and a removable, extendible secondary visor. A first set of securing snaps will hold the secondary visor in place adjacent to the primary visor. The secondary visor is extended by unsnapping the visor from the first set of snaps, moving the visor to a second, extended position, and then attaching the visor to a second set of securing snaps. This patent, similar to the Kirshner patent discussed above, merely extends the length of the visor in an attempt to solve the problem of protecting the eyes from excessive sunlight.

SUMMARY OF THE INVENTION

The present invention is a dual-visor hat worn about the head of an intended user. This invention includes one stationary visor portion and a second visor which is adjustable relative to the stationary visor.

The present invention comprises a substantially circular headband. A generally stationary visor connects to the front portion of the headband. Normally, when the intended user wears the hat the headband is in position about the head and above the ears, and the stationary visor projects outwardly from the headband above the eyes of the user.

The generally stationary visor has a flexible, crescent-shaped, air permeable material attached along one longitudinal edge of the visor. This crescent shaped material has a second longitudinal edge oppositely spaced from the first edge and extending downward from the juncture of the headband and stationary visor.

A second visor disposed beneath the generally stationary visor has one edge connected along the crescent shaped material's second edge. The second visor is detachably secured to the first visor by a hook-and-loop type material that will facilitate quick release of the second visor from the first visor.

The second visor when disposed in a first, detached position will extend the flexible material whereby the second visor will be angularly positioned downward relative to the face and eyes of the intended user. In this first position the second visor will provide additional shade for the eyes of the user. In addition, in this position the flexible material fits snugly against the user's forehead, enhancing the capability of the hat to be retained on the head of the user. The second visor when disposed in a second position will fold the flexible crescent shaped material into an accordion shape, suitable for storing between the first and second visors.

The present invention may include means for sizing the headband to the head of the intended user by an adjustable hook-type fastening material or clasp positioned opposite from the first visor and disposed within the headband. The fastener may be opened, to separate the headband and to allow the headband to be placed about the head of the user. The separated ends are then joined at the rear of the head of the user. Adjusting the fastener will increase or decrease the size of the headband.

In the eventuality that the present invention is to be worn in gusty winds, an elastic chin strap may be provided. The chin strap, when not in use, is stored in an overlying relation on top of the first visor. If desired, the chin strap may be moved from its stored position and placed under the chin of the user, thereby retaining the hat on the head of the user.

Although the hat of the present invention may be open above the headband to expose the crown of the head and provide for ventilation of the crown, it will be understood that the hat may take the conventional form wherein the crown of the head is covered, as is shown in U.S. Pat. No. 2,462,258 to Dannenberg, the disclosure of which is incorporated herein by reference for all purposes.

Further advantages of the present invention will be readily apparent to those skilled in the art and from the following detailed description, taken in conjunction with the annexed sheets of drawings.

DETAILED DESCRIPTION OF THE PREFERRED EMBODIMENT

Figure 1:
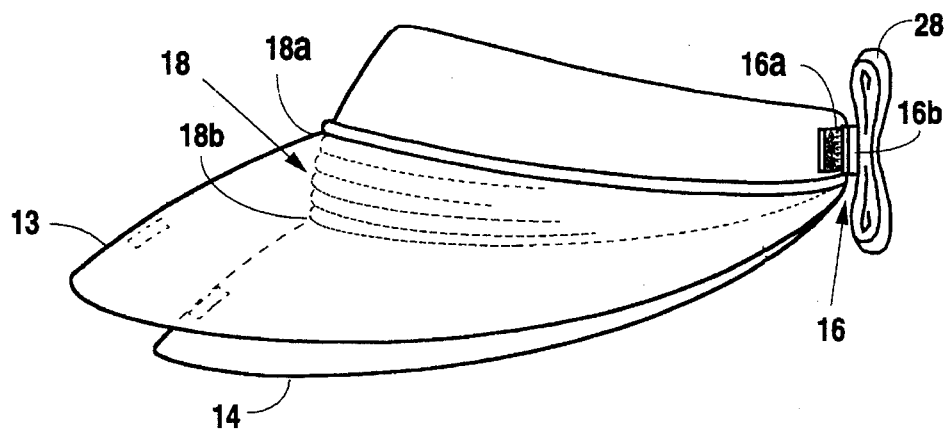
FIG. 1 is a side elevation view of a dual visor hat.

The preferred embodiment of the present invention is a dual visor hat illustrated generally at 10 of FIG. 1. The dual visor hat 10 comprises a generally circular headband member 12 with visors 13 and 14 connected thereto and projecting outward and downward from headband member 12. Headband member 12 is intended to be worn about the head of an intended user with visors 13 and 14 extending outward from headband member 12 above and partially shading the eyes of the user from excessive sunlight. Hat 10 may, if desired, be sized to be worn by adults or children.

To accommodate the varying head sizes of adults and children a hook-and-loop type adjustable fastener 16 is provided. Fastener 16 is disposed within headband member 12 and opposite from visors 13 and 14. Fastener 16 comprises a first foam-like material 16b connected to one end of headband member 12. Fastener 16 has hook-type material 16a connected to the opposite end of headband member 12. To adjust hat 10 to the head of the user, headband member 12 is placed about the head of the user and loop-type fastening material 16b is positioned to abut hook-type material 16a. Pressure applied to the outer surfaces of the two abutting materials 16a and 16b, engages their respective surfaces. Hat 10 is now adjustably secured and sized to the head of the user. Example of fastener 16, inserted to the rear of headband member 12, securing hat 10 about the head of the user would employ mating members of VELCRO® fastening material. One half of the first mating member of VELCRO® fastening material would mate to the second half of VELCRO® fastening material thereby positionally adjusting the Velcro® strips to size hat 10 to the head of the user. A decorative bow 28 may, if desired, be added to headband member 12 covering fastener 16 in the closed position of headband member 12.

Figure 3:
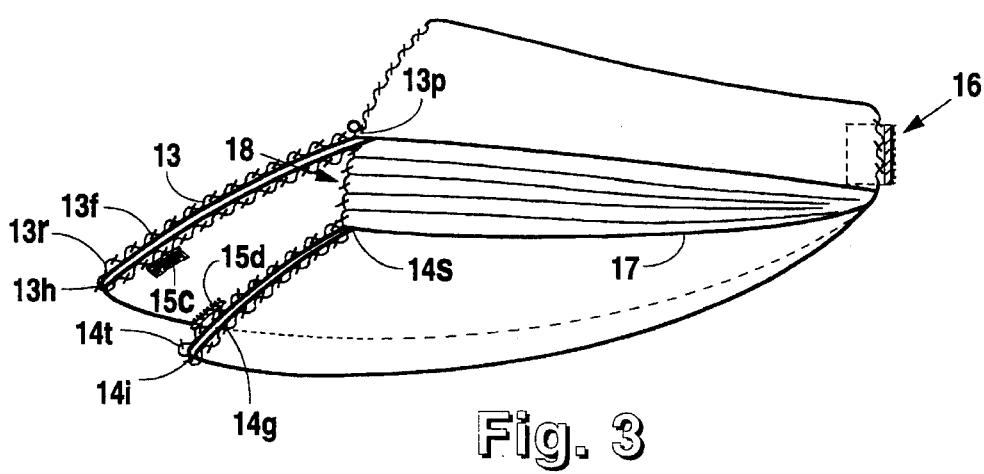
FIG. 3 is a sectional view at section 3—3 of FIG. 2.

Referring now to FIG. 3, first visor 13 has a proximal end 13p and a distal end 13r relative to headband member 12. First visor 13 comprises a substantially rigid inner member 13h. Inner member 13h has its top and bottom surfaces covered with a sheet member 13f. Sheet member 13f may, if desired, be cloth sewn or glued to the top or bottom surfaces of inner member 13h. First visor 13 now has a top surface 13k, FIG. 5 and bottom surface 13l, FIG. 3 comprising inner member 13h covered by sheet member 13f.

Second visor 14 has a proximal end 14s and a distal end 14t relative to headband member 12. Second visor 14 comprises a substantially rigid inner member 14i. Inner member 14i has its top and bottom surfaces covered with a sheet member 14g. Sheet member 14g may, if desired, be the same or different material that covers first visor 13, and that material may be sewn or glued to the top or bottom surfaces of inner member 14i. Second visor 14 now has a top surface 14m, FIG. 6, and a bottom surface 14n, FIG. 4, comprising inner member 14i covered by sheet member 14g.

Figure 2:
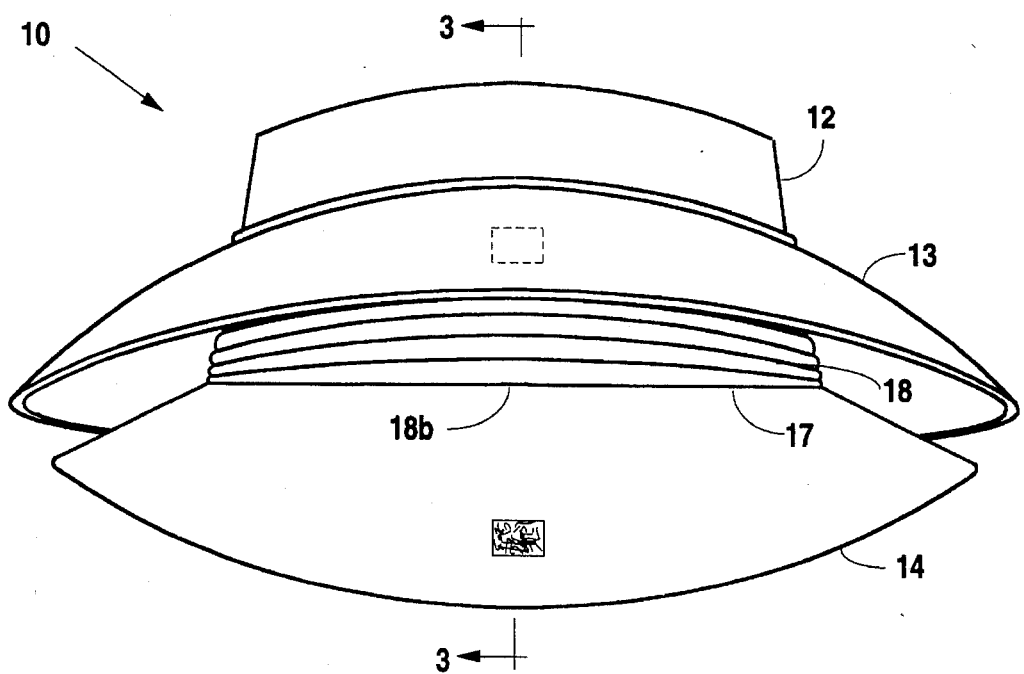
FIG. 2 is a front view of FIG. 1.

FIG. 2 illustrates the proximal end 13p of first visor 13 connected to headband member 12 with first visor 13 projecting outward and generally sloping downward from headband member 12. A foldable, crescent-shaped member 18 has one longitudinal edge 18a connected to the bottom surface 13l of first visor 13 along juncture 29, FIG. 7. Crescent-shaped member 18 has a second longitudinal edge 18b oppositely spaced from first edge 18a. Second edge 18b is connected to the top surface 14m of second visor 14 along juncture 17.

Figure 4:
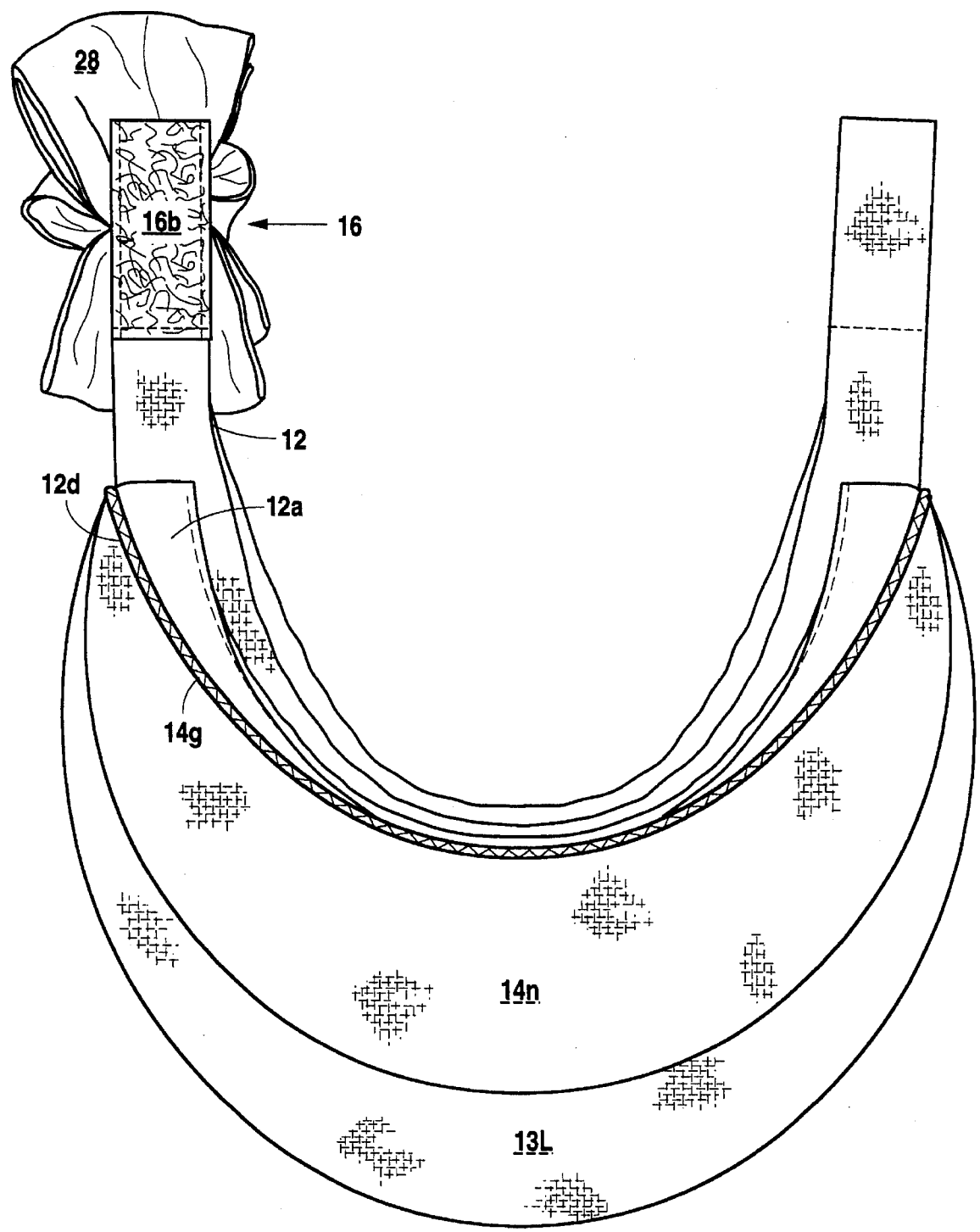
FIG. 4 is a bottom view of FIG. 1.
Figure 6:
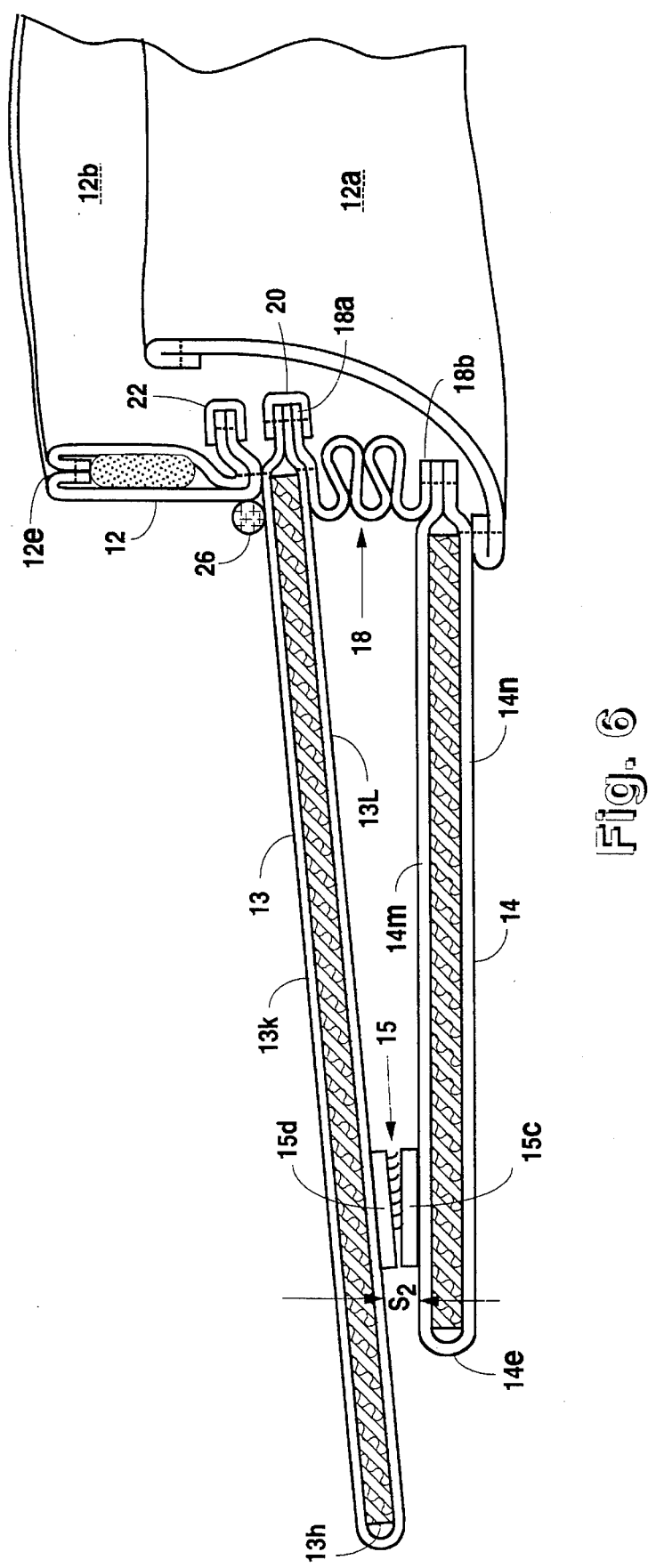
FIG. 6 is a sectional view of FIG. 5 at section 6—6 illustrating the dual visor hat in a closed position.

Referring to FIG. 4, first visor 13 is shown overlying second visor 14 in a closed position. In FIG. 6, second visor 14 in the closed position is detachably secured to the bottom surface 13l of first visor 13 by a hook-and-loop type fastener 15. Fastener 15 comprises loop-type material 15d secured in proximity to distal end 13r of first visor 13, FIG. 3. Fastener 15 has hook-type material 15c secured in proximity to distal end 14t of second visor 14. Fastener 15's components 15c and 15d are axially aligned on their respective visors. Securing second visor 14 to first visor 13 is very similar to the operation of fastener 16 discussed above wherein pressure is applied to opposing visors 13 and 14 engaging components 15c and 15d of fastener 15, thereby detachably securing second visor 14 to first visor 13.

Figure 7:
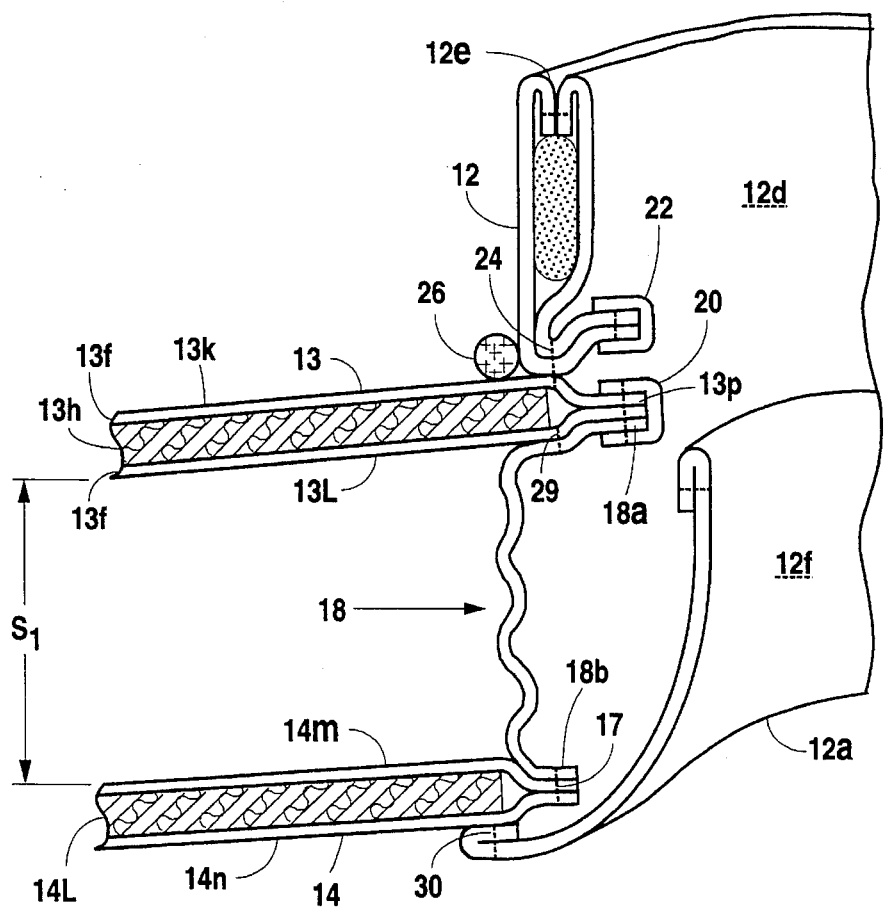
FIG. 7 is a sectional view of FIG. 5 at section 6—6 illustrating the dual visor hat in an open position.

Referring now to FIG. 7, hat 10 has a moisture absorbent liner 12a connected to the bottom surface 14n along juncture 30 of second visor 14. Liner 12a extends upward and is spaced from the inner surface 12d of headband member 12. Liner 12a has one surface 12f facing towards the forehead of the user. Liner 12a extends substantially along the circumference of headband member 12, FIG. 4.

Second visor 14 is illustrated beneath and adjacent to first visor 13 with crescent-shaped member 18 in an unfolded first position $s_1$. This first position extends second visor 14 downward from first visor 13. FIG. 6 illustrates crescent-shaped member 18 in a folded second position $s_2$. The second position will allow crescent-shaped member 18 to be folded in an overlying accordion shape to be stored between first visor 13 and second visor 14. Second visor 14 is disposed in detachably securable and moveable relation with first visor 13.

In FIG. 7, a first elongated flexible sheet member 20 is foldable across the width of the connection defined by the proximal end 13p of first visor 13 and the connection to edge 18a of crescent-shaped member 18. Sheet member 20 has its perimeter edges secured along the connection defined by the proximal end 13p of first visor 13 and the first edge 18a of crescent-shaped member 18.

A second elongated flexible sheet member 22 is foldable across the width of the connection defined by inner surface 12d that has its prerimeter edges sewn to outer surface 12e. Headband member 12 is sewn in proximity to the proximal end 13p of the top surface 13k of first visor 13 along juncture 24. Second sheet member 22 is disposed in an overlying relation with first sheet member 20.

Figure 5:
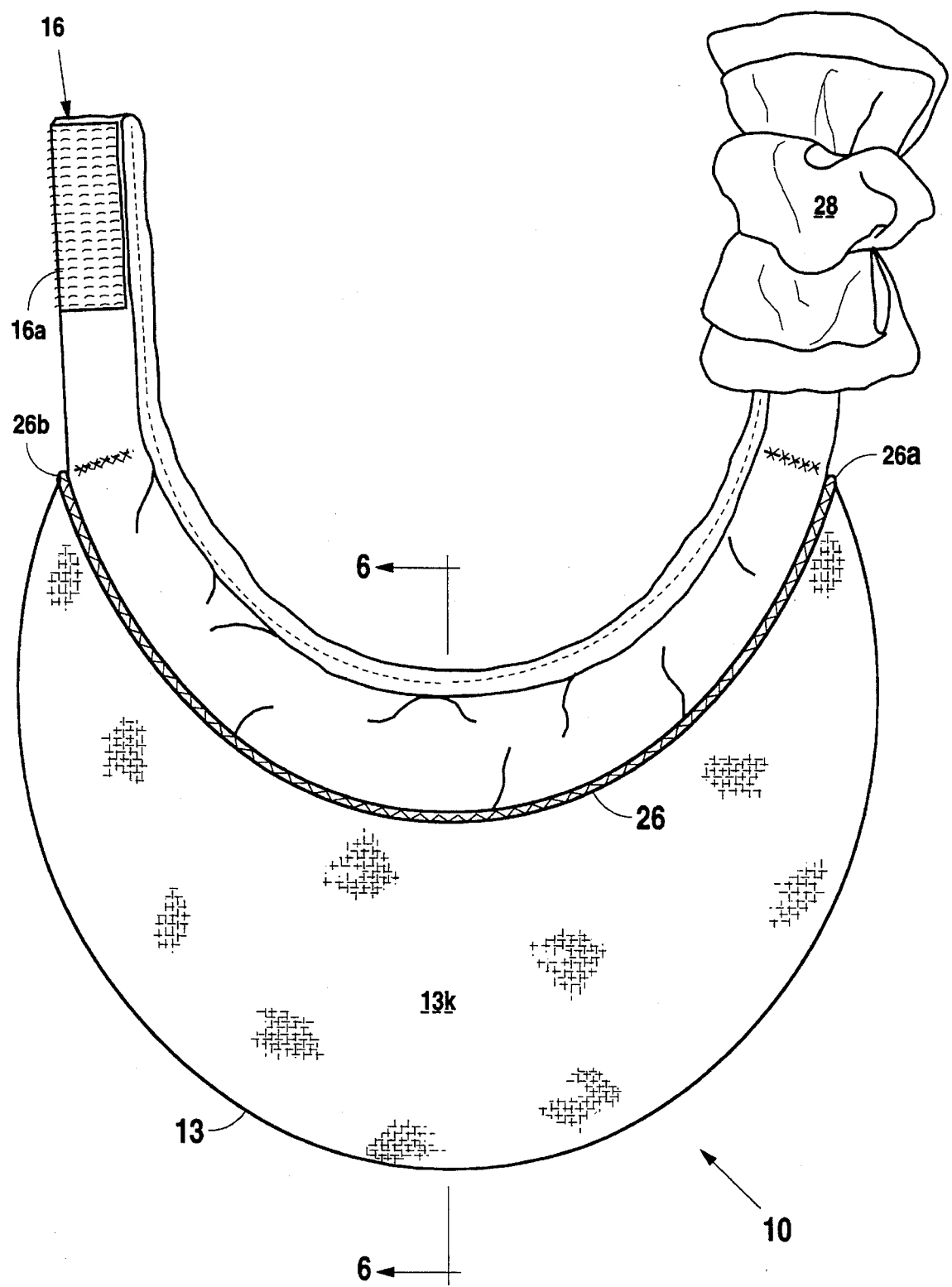
FIG. 5 is a top view of FIG. 1.

Referring to FIG. 5, hat 10 has an elongated retaining strap 26 disposed in a first position in an overlying relation with first visor 13. Retaining strap 26 is elastically deformable and is joined at its end points 26a and 26b to headband member 12. Retaining strap 26 may be disposed in a second position under the chin of the intended user of the hat whereby the hat is secured onto the head of the intended user.

Figure 8:
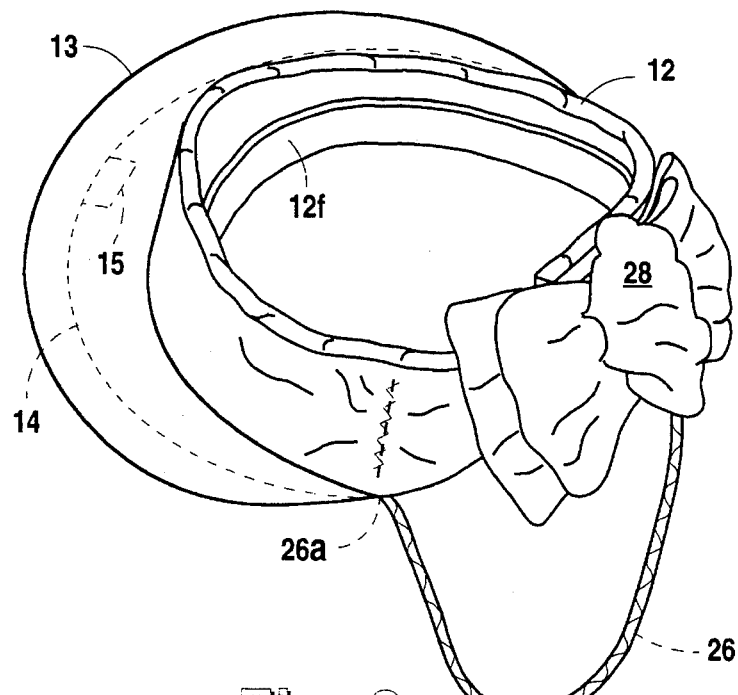
FIG. 8 is a perspective view of the dual visor hat.

Referring now to FIG. 8, retaining strap 26 is shown having been moved from its first position overlying first visor 13 to its second position extending downward and to the rear of hat 10. Retaining strap 26 in this second position will accommodate the chin of the user thereby retaining hat 10 on the head of the user. Retaining strap 26 may, if desired, be fabricated from any type of elastically deformable material that will allow retaining strap 26 to be moved from its first position to its second position under the chin of the user. Examples of that type of material are rubberized cloth or woven cloth.

Headband member 12 may be disposed about the head of the user with first visor 13 and second visor 14 extending outward from headband member 12 above and partially shading the eyes of the user. The user may, if desired, disengage second visor 14 from first visor 13 and allow second visor 14 to descend to a position determined by the width of crescent shape member 18. In this position second visor 14 will further shade the eyes of the user from excessive sunlight. If desired, crescent-shaped member 18 may be of selected width. Once this desired width is selected and the material is attached to the visors, second visor 14 may be adjusted relative to first visor 13 to accommodate various degrees of shade desired by the user of the present invention.

The invention now being fully described, it would be apparent to one of ordinary skill in the art that many changes and modifications can be made thereto without departing from the spirit and scope of the invention as set forth herein.

I claim:

1. An adjustable, dual-visor hat, comprising:

A first substantially rigid visor;

a second substantially rigid visor disposed adjacent to said first visor;

a flexible member secured to the first and second visors to position the first and second visors adjacent each other when said flexible member is in a folded position and spaced from each other when said flexible member is in an unfolded position.

2. An adjustable, dual-visor hat, comprising:

a generally circular headband member;

a first visor having top and bottom surfaces, said first visor being connected at its top surface to the headband member;

a flexible member having a first longitudinal edge connected to the bottom surface of the first visor;

said flexible member having a second longitudinal edge oppositely spaced from said first edge; and a second visor having a top surface, said second visor disposed adjacent to said first visor and connected at its top surface to the second edge of the flexible member.

3. The dual-visor hat of claim 2, further comprising means for sizing said headband member to the head of an intended user.

4. The dual visor hat of claim 3, wherein the means for sizing comprises a hook-and-loop type fastener oppositely spaced from said first visor.

5. The dual-visor hat of claim 2, further comprising means for absorbing moisture from the forehead of an intended user.

6. The dual-visor hat of claim 2 wherein the flexible member is foldable along its length.

7. The dual-visor hat of claim 6, further comprising means for detachably securing said first visor adjacent said second visor.

8. The dual-visor hat of claim 2, further comprising means for retaining the hat on the head of an intended user.

9. The dual-visor hat of claim 8, wherein the means for retaining comprises an elongated strap having its end points connected to said headband member, said strap overlying said first visor's top surface when in a first position, and said strap being disposed under the chin of an intended user when in a second position.

10. The dual-visor hat of claim 9, wherein said strap is elastically deformable.

11. An adjustable, dual-visor hat, comprising:

a generally circular headband member;

a first visor having top and bottom surfaces, said first visor being connected at its top surface to the headband member;

a flexible member having a first longitudinal edge connected to the bottom surface of the first visor, said flexible member being foldable along its length;

said flexible member having a second longitudinal edge oppositely spaced from said first edge;

means for detachably securing said first visor adjacent said second visor;

a hook-and-loop type fastener oppositely spaced from said first visor for sizing said headband member to the head of an intended user;

means for absorbing moisture from the forehead of an intended user; and an elastically deformable, elongated strap having its end points connected to said headband member, said strap overlying said first visor's top surface when in a first position, and said strap being disposed under the chin of an intended user when in a second position for retaining the hat on the head of the intended user.

* * * * *